United States Patent [19]

Bennett

[11] Patent Number: 5,236,334
[45] Date of Patent: Aug. 17, 1993

[54] CORE BIOPSY NEEDLE UNITS FOR USE WITH AUTOMATED BIOPSY GUNS

[76] Inventor: Lavon L. Bennett, 130 W. Center, Alpine, Utah 84004

[21] Appl. No.: 807,498

[22] Filed: Dec. 16, 1991

[51] Int. Cl.$^5$ ............................................. A61B 10/00
[52] U.S. Cl. ................................................... 128/754
[58] Field of Search ...................... 128/749, 751, 754; 606/167, 170, 171

[56] References Cited

U.S. PATENT DOCUMENTS

| | | | |
|---|---|---|---|
| 4,917,100 | 4/1990 | Nottke | 128/754 |
| 5,036,860 | 8/1991 | Leigh et al. | 128/754 |
| 5,127,419 | 7/1992 | Kaldany | 128/754 |

Primary Examiner—Max Hindenburg
Attorney, Agent, or Firm—Terry M. Crellin

[57] ABSTRACT

Core biopsy needle units used with automated biopsy guns are disclosed. The needle units comprise an elongate solid needle having a notch formed adjacent to the end of the needle. A hub is securely attached to the other end of the needle. An elongate cannula is received over the notched end of the needle such that the needle slides longitudinally through the cannula. A second hub is securely attached to the first end of the cannula, and engagement means are formed in the hub on the needle. The hub on the needle and the second hub on the cannula are adapted to be received in respective receiver cavities of an automated biopsy gun, with the engagement means in the hub on the needle making firm, releasable, interlocking engagement with corresponding engagement means associated with the receiver cavity in which the hub on the needle is received. In addition, a mechanism is provided for releasably interlocking the needle and cannula at a proper position and orientation for insertion into the receiver cavities of an automated biopsy gun. The mechanism is released once the needle unit is properly received in the biopsy gun to allow telescopic movement of the needle within the cannula.

12 Claims, 2 Drawing Sheets

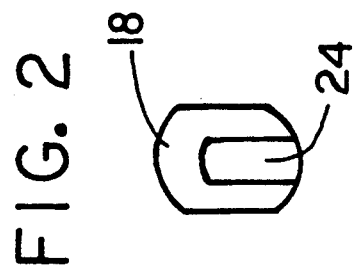
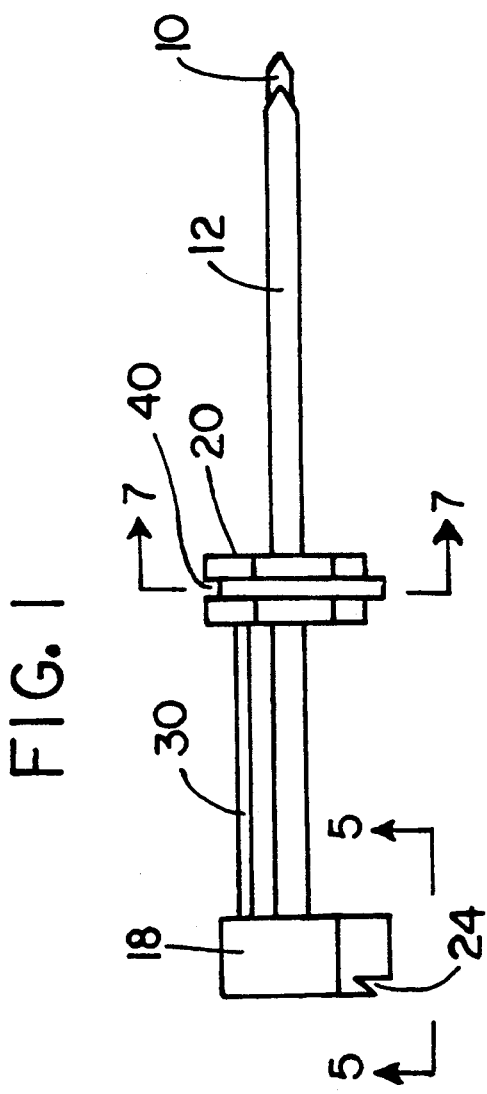
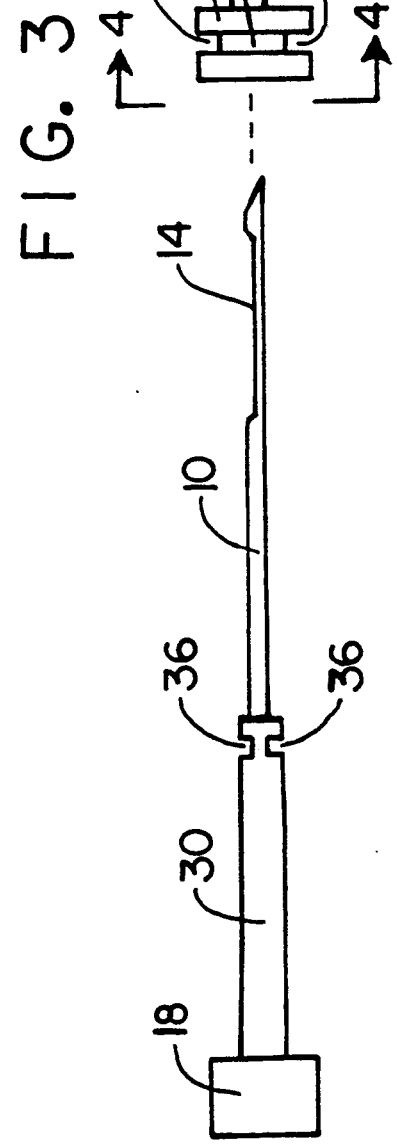

CORE BIOPSY NEEDLE UNITS FOR USE WITH AUTOMATED BIOPSY GUNS

BACKGROUND OF THE INVENTION

1) Field of the Invention

This invention relates to improvements in needle units used with automated biopsy guns of the type which can be adjusted to allow precise amounts of sample tissue to be collected during a biopsy procedure.

2) Prior Art

The removal of minute tissue samples from humans and animals by introducing a needle into the body and catching the sample within the needle, is a frequently used medical practice today. Such samples are necessary for microscopic examination, organ cultures, etc.

The method most commonly followed for obtaining tissue samples has been to use a needle which is formed of an inner solid rod which has a sampling notch in the distal end thereof, in conjunction with a hollow outer cannula which slides thereover and cuts tissue which has been located in the sampling notch of the inner rod. The inner rod, except for its pointed distal end, is located within the cannula when the device is inserted into the tissue to be sampled. The outer cannula is then held stationary while the inner rod is inserted deeper into the tissue. While in this position, tissue moves into the sampling notch of the inner rod just adjacent the pointed distal tip thereof. The inner rod is then held stationary while the outer cannula is slid thereover. Motion of the outer cannula passing over the sampling notch causes the tissue located therein to be severed from surrounding tissue and thereafter to be trapped in the sampling notch as the cannula completely covers the inner needle distal end. Both the outer cannula and the inner rod with the tissue sample secured therein are then simultaneously removed from the patient. The outer cannula is then slid back away from the distal end of the inner rod to allow removal of the tissue sample from the sampling notch thereof. The tissue sample is then examined.

This general method of tissue sampling has been used for several decades and is exemplified in U.S. Pat. No. 3,477,423. As disclosed therein, the needle movements are made manually. This has certain disadvantages, in that movements may not be made fast enough to insure clean and complete severance of a tissue sample. Further, manual operation of the needle generally involves inaccurate movements, and slight lack of coordination between the needle and the cannula. This often causes unnecessary tissue damage and, in the case of infectious or tumorous tissue, can possibly cause spreading of the diseased tissue throughout a larger tissue area. Also, during manual operation of a needle, the patient may move slightly during the introduction thereof into the tissue and cause the needle to miss its target area. Also, respiratory movements are common for some organs, for example the liver and the kidney, which further may reduce the accuracy of the sampling technique.

An improvement in the above mentioned method of biopsy sampling has been to restrict needle movements by containing the inner rod and outer cannula inside a holder or automated biopsy gun. The biopsy gun restricts needle movement to specific directions and also carries springs and separate piston mechanisms therein which drive the rod and cannula through their sampling motions in a rapid and predictable manner. This technique is exemplified in U.S. Pat. No. 4,699,154. Even though these automated biopsy guns are an improvement over manually actuated needles, they nevertheless have several disadvantages. For example, the length of the needle movement of the conventional automated biopsy guns cannot be adjusted according to the size of the sample desired to be taken. Therefore, unnecessary quantities of tissue may be removed from the tissue sample area causing unnecessary tissue damage and possibly unnecessary spreading of diseased tissue. Further, the forceful introduction of a needle into the tissue area generally causes a certain amount of damage to the tissue in the immediate surroundings of the target area. This is due to the high pressure released from the needle in the injection process.

In my copending U.S. patent application Ser. No. 07/542,324 there is disclosed an improved automatic biopsy gun which allows controlling of the size of a tissue sample taken by the biopsy needle. With the improved biopsy gun, the size of the sample does not exceed the necessary amount of tissue needed for diagnostic purposes. Also, a smaller tissue target area, such as a lesion or tumor or the like can be sampled with a shorter movement of the needle and a smaller and more controlled sample size is taken. This prevents the needle from passing through the target area into unaffected area of the tissue, nor does the needle reach outside of the organ, tumor, lesion, etc. which is being sampled to thereby cause risk of damage to other structures such as adjacent large blood vessels or the like.

With the development of the improved automated biopsy gun, it has been found advantageous to further develop improved needle units to be used with the improved gun. Needle units used with conventional automated biopsy guns comprised an inner needle with a hub attached at one of the ends of the needle. An outer cannula fit over the needle, and another hub was attached to the end of the cannula corresponding to the end of the needle having a hub.

The respective hubs were inserted in mutually respective receiver cavities in the automated biopsy gun. This required a somewhat complicated manual manipulation of the two hubs at a precise spaced apart distance so that the hubs could be inserted int their respective receiver cavities in the automated biopsy guns. In addition, the hubs had to be rotated and oriented in a proper orientation relative to each other for proper placement in the receiver cavities.

Further, with the improved biopsy guns of my copending U.S. application Ser. No. 07/542,324, controlled movement of the piston of the biopsy gun which contacts and therefor drives the hub of the needle is used to control movement of the needle. However, with conventional needle units, the needle itself contributed to uncontrolled movement. This uncontrolled movement occurred primarily when the improved automated biopsy gun was set to achieve a limited movement of the needle, i.e., a movement of the needle which is less than the longest possible movement. In such instances, there was no positive means of preventing further floating movement of the needle especially during the stage of the operation in which the cannula was being moved.

OBJECTS AND SUMMARY OF THE INVENTION

It is an object of the present invention to provide improved core biopsy needle units for use with automated biopsy guns, wherein the needle units have means associated therewith for holding the hubs of the needle and cannula in a fixed position with proper spacing and orientation to be quickly and easily inserted into the respective receiver cavities of the automated biopsy gun, with further means for releasing the hubs from being held in their fixed positions when the hubs are properly received and positioned in their respective receiver cavities. The release of the hubs once they are properly received in the receiver cavities of the biopsy gun allows the hubs to move independently of each other as is required for operation of the biopsy gun.

It is further an object of the present invention to provide improved core biopsy needle units to be used with automated biopsy guns wherein the hubs on the needle portion of the needle units are provided with integral engagement means incorporated into the hubs, whereby the engagement means can interlock with respective pistons of the automated biopsy guns when the hubs of the needle units are received in the receiver cavities of the biopsy guns such that the hubs on the needle portions become firmly attached to the respective pistons of the biopsy guns and thus move in precise, controlled movement corresponding to the movement of the pistons.

These and other objects of the present invention are embodied in novel improvements in needle units used with automated biopsy guns as will be described fully in the detailed description following hereafter. Briefly, the first objective mentioned above is accomplished by providing a needle unit comprising an elongate solid needle having a notch formed therein nearer one end of the needle than the other end. Preferably, the notch is located adjacent to one of the ends of the needle and that end is formed with a sharp point. An elongate cannula is received over the sharpened end of the needle such that the needle can slide longitudinally through the cannula, with the sharpened end of the needle projecting from the other end of the cannula.

A first hub is securely attached to the end of the needle opposite its sharpened end, and a second hub is securely attached to the end of the cannula that approaches the first hub on the needle as the needle is received longitudinally within the cannula. To maintain these two hubs in proper fixed positions spaced apart from each other and in proper orientation with each other, an elongate, essentially straight arm extends from the hub on the needle. The arm is integrally attached at is first end to the hub on the needle and projects from the hub so as to be essentially parallel with the needle.

Means are provided for interlocking the second end of the arm to the second hub to hold the second hub at the desired, fixed distance and at a desired, fixed orientation with respect to the first hub. With the two hubs being held in fixed position, the needle unit can be quickly and easily attached to an automated biopsy gun, with the two hubs being received in the respective receiver cavities of the biopsy gun.

Additional means are associated with the second hub of each needle unit for releasing the interlocking engagement between the hubs when the hubs are properly received in the receiver cavities of the automated biopsy gun. This allows the hubs and thus the needle and cannula to move independent of each other as is required during the operation of the automated biopsy gun.

The second objective mentioned above is accomplished by providing a needle unit comprising the notched needle, the cannula and the hubs associated with the needle and cannula as described previously. Engagement means are formed in the hub on the needle, with the engagement means being positioned adjacent to the side of the hub facing away from the needle. When the hub on the needle is received in its respective receiver cavity of an automated biopsy gun, the engagement means on the hub makes firm, releasable, interlocking engagement with corresponding engagement means associated with the piston in the receiver cavity such that the hub is firmly but releasably secured to the piston.

With the hub on the needle firmly attached to the piston of the automated biopsy gun, the needle will move in precise, controlled movement corresponding exactly to the movement of the piston of the automated biopsy gun. Examples of automated biopsy guns with which the improved needle units of the present invention can be used are illustrated and described in my copending U.S. patent application Ser. No. 07/542,324. the entire contents of which is incorporated herein by reference.

Additional objects and features of the present invention will become apparent from the following detailed description taken together with the accompanying drawings.

THE DRAWINGS

FIG. 1 is a side elevation of an improved core biopsy needle unit in accordance with the present invention.

FIG. 2 is an end view of the needle unit of FIG. 1 taken from the left end of the unit as shown in FIG. 1;

FIG. 3 is an exploded top view of the needle unit of FIG. 1 showing the cannula and needle separated from each other for clarity and further showing the sliding engagement member removed from the hub on the cannula;

DETAILED DESCRIPTION OF THE ILLUSTRATED EMBODIMENTS

Figure 5:
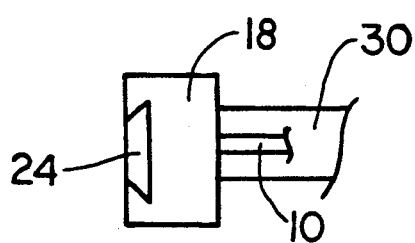
FIG. 5 is a bottom view of the hub on the needle as taken along line 5—5 of FIG. 1.

As shown in the drawings, the improved core biopsy needle unit of the present invention an elongate solid needle 10 and an elongate cannula 12 that slides in telescopic fashion over the needle 10. A notch 14 is formed in the needle 10 nearer a first end of the needle 10 than the second end thereof. Preferably, as illustrated, the notch 14 is located closely adjacent to the first end of the needle 10. The first end of the needle 10 is sharp pointed as is customary to facilitated insertion of the needle and cannula through the tissue of the patient who is undergoing a biopsy.

A hub 18 is securely attached to the second end of the needle 10, and the elongate cannula 14 is adapted to slide over the first end of the needle 10 such that the needle 10 slides longitudinally through the cannula 12 as best shown in FIG. 1. A second hub 20 is securely attached to the first end of the cannula 12, i.e., the end that is introduced over the sharpened first end of the needle 10.

The hub 18 and the second hub 20 are adapted to be received in respective receiver cavities of an automated biopsy gun. The automated biopsy gun with the receiver cavities is not shown in the drawings. Such an automated biopsy gun is shown in my copending U.S. patent application Ser. No. 07/542,324, and the entire disclosure in that application is incorporated herein by reference.

One of the principal advantages of the improved biopsy guns as disclosed in my copending U.S. patent application Ser. No. 07/542,324 is that the driving means for moving the hub 18 on the needle 10 is adapted to control the movement of the hub 18 and needle 10 to any specific degree of the total possible length of movement thereof. As mentioned previously when the needle of a conventional needle unit is moved by such an improved biopsy gun in an amount less than the total possible movement, the needle can float and move in an undesired movement when the cannula moves.

In accordance with the present invention, engagement means are provided in the hub 18 for making firm, releasable, interlocking engagement with corresponding engagement means associated with the receiver cavity of the automated biopsy gun in which the hub 18 is received. By making positive, interlocking engagement with the driving means of the automated biopsy gun, the hub 18 and needle 10 are restricted to the exact movement of the driving means and cannot float and move in undesired movement during subsequent movement of the cannula 12.

As illustrated in FIGS. 1, 2 and 5 of the drawings, in one embodiment of the improved core biopsy needle units in accordance with the present invention, the engagement means formed in the hub 18 comprises a mortise 24 cut into the side of the hub 18 facing away from the needle 10. As shown in FIGS. 1, 2 and 5 of the drawings, the mortise 24 comprises an elongate slot cut upwardly into the side of the hub 18 from the lower end of the hub 18. The slot extends only part way up along the side of the hub 18 and does not extend to the upper end of the hub 18. The sides and top edges of the slot forming the mortise 24 are incut to form a dovetail. With the mortise 24 as shown in FIGS. 1, 2 and 5, the corresponding engagement means on the driving member of the automated biopsy gun would be a tenon that would slide into engagement with the mortise 24.

Figure 6:
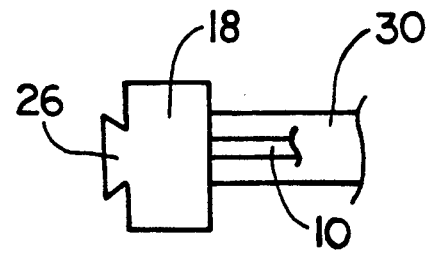
FIG. 6 is a view similar to that of FIG. 5 but showing a variation in the engagement means wherein the mortise of the hub of FIG. 5 has been replaced by a tenon.

As shown in FIG. 6, another embodiment of engagement means is formed in the hub 18. In this embodiment, the engagement means comprises a tenon 26 projecting from the side of the hub 18 facing away from the needle 10. The tenon 26 has incut longitudinal sides that are adapted to slide into a corresponding mortise in the corresponding engagement means in the driving member of the automated biopsy gun. Although specific shapes of the mortise 24 and tenon 26 which form the engagement means on the hub 18 have been illustrated, it should be recognized that the mortise 24 and tenon 26 could have various other shapes.

As was mentioned previously, with the conventional automated biopsy guns as well as with the improved biopsy guns of my copending U.S. patent application Ser. No. 07/542,324, the hubs on the needle and cannula of the prior art needle units had to be hand manipulated and held in precise orientation and spaced relationship when being attached to the biopsy gun. The hubs had to be held at a precise distance from each other to fit into the receiver cavities of the biopsy gun, and the hubs had to be maintained in a specific rotational orientation with each other. This complicated manual manipulation was time consuming and not appreciated by surgeons using the biopsy guns.

In accordance with the present invention improved core biopsy needle units are provided which have an elongate solid needle 10 with a notch 14 therein as described above. Also as described above, a hub 18 is attached to the needle 10 and a second hub 20 is attached to the cannula 12. The cannula 12 is received over the needle 10 for telescopic movement as also fully described previously. In accordance with a preferred embodiment of the present invention, the needle units are further provided with an elongate, straight arm 30 whose first end is integrally attached to the hub 18 and whose second end extends away from the hub 18 so that the arm 30 projects from the hub 18 in essentially parallel orientation to the elongate needle 10 extending from the hub 18.

Means are further provided for interlocking the second end of the arm 30 to the second hub 20 to hold the second hub 20 at a fixed distance and at a fixed orientation with respect to the first hub 18. The second hub 20 has means associated therewith for releasing the interlocking engagement when the second hub 20 is properly received in a receiver cavity of an automated biopsy gun.

Figure 4:
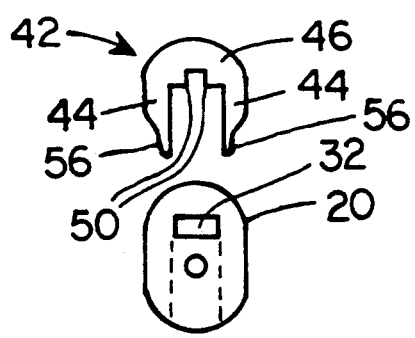
FIG. 4 is an end view of the hub on the cannula as taken along line 4—4 of FIG. 3, with the sliding engagement member being shown in exploded position above the hub.

In the preferred embodiment illustrated in the drawings, the means for interlocking the second end of the arm 30 to the second hub 20 comprises an opening 32 (see FIGS. 4 and 7) through the second hub 20. As illustrated, the arm 30 has a rectangular cross section and the opening 32 has a shape corresponding to the cross section of the arm 30, such that the arm 30 can be received through the opening 32 for longitudinal sliding motion through the opening 32. This allows the hub 18 to move toward the hub 20, with the arm 32 sliding through the opening 32 in the hub 20. As the hub 18 moves through the hub 20, the needle 10 moves in telescopic movement through the cannula 12.

At least one notch 36 is provided on the perimeter of the arm 30 adjacent to the second end of the arm 30. Preferably, as illustrated, two oppositely facing notches 36 are provided in the arm 30 A generally inverted, U-shaped slideway is formed in the second hub 20. The slideway comprises a pair of elongate slots 38 formed in the opposite sides of the second hub 20 and a third slot 40 formed at the top of the second hub 20 so as to interconnect the pair of slots 38 on the sides of the second hub 20.

A generally U-shaped slide member 42 slides in the slideway. The slide member 42 comprises a pair of legs 44 spaced from each other by a base member 46 attached to respective ends of the legs 44. The legs 44 of the slide member 42 are received in longitudinal sliding engagement in the pair of elongate slots 38 in the second hub 20, and the base member 46 of the slide member 42 is received in transverse sliding engagement in the third slot 40 formed at the top of the second hub 20.

Figure 7:
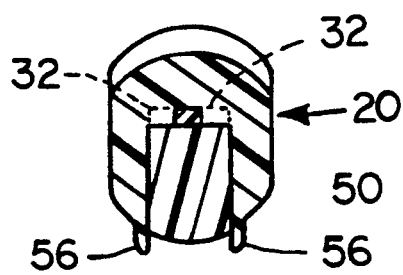
FIG. 7 is a cross section through the assembled needle unit of FIG. 1 taken along line 7—7 of FIG. 1.

At lease one interlock tab 50 is provided on the base member 46 of the U-shaped slide member 42. As shown in the drawings, two tabs 50 are provided by cutting a notch inwardly on the inside of the base member 46 of the slide member 42. These tabs 50 engage and interlock with the notches 36 on the perimeter of the arm 30 when the notches 36 are aligned with the third slot 40 of the slideway and when the U-shaped slide member is slid so that the interlock tabs 50 slide into engagement with the notches 36 as best shown in FIG. 7.

When the interlock tabs 50 of the slide member 42 of the second hub 20 engage the notches 36 in the arm 30, the hubs 18 and 20 are maintained in stable fixed position, being spaced from each other by a set distance and also being locked in a set rotational orientation with respect to each other. The set spaced distance between the hubs 18 and 20 and the proper orientation of the hubs 18 and 20 allow the needle unit to be quickly and easily attached to an automated biopsy gun. The hubs 18 and 20 are simply inserted into place in the receiver cavities of the automated biopsy gun.

Once the hubs 18 and 20 of the needle unit are properly placed in the receiver cavities of the automated biopsy gun, means are advantageously provided for automatically releasing the interlocking engagement of the second end of the arm 30 to the second hub 20 so that the hubs 18 and 20, and thus the needle 10 and cannula 12, can move freely relative to each other.

In the preferred illustrated embodiment, the means for releasing the interlocking engagement of the arm 30 and the second hub 20 comprises at least one foot member 56 (two such members 56 being shown in the illustrated embodiment) extend downwardly from one of or both of the legs 44 of the slide member 42. When the U-shaped slide member 42 is slid so that the interlock tabs 50 slide into engagement with the notches 36, the foot members 56 extend from a lower side of the second hub 20. When the second hub 20 is received in a respective receiver cavity of an automated biopsy gun, the foot members which are otherwise extending from the lower side of the second hub 20 are pushed upwardly by the receiving cavity. The U-shaped slide member 42 is in turn pushed upwardly so that the interlock tabs 50 slide out of engagement with the notches 36 in the arm 30, and the arm 30 can then slide freely in the opening 32 of the second hub 20.

Although preferred embodiments of needle units of the present invention have been illustrated and described, it is to be understood that the present disclosure is made by way of example and that various other embodiments are possible without departing from the subject matter coming within the scope of the following claims, which subject matter is regarded as the invention.

I claim:

1. Improved core biopsy needle units used with automated biopsy guns, said needle units comprising
    an elongate solid needle having a first and second end;
    a notch formed int he needle nearer said first end of the needle than the second end thereof;
    a hub securely attached to the second end of said needle, said hub having an exposed end facing away from the second end of said needle;
    interlocking type engagement means formed in the exposed end of the hub that faces away from the second end of said needle;
    an elongate cannula having a first and second end, with said first end being received over said first end of said needle such that the needle slides longitudinally through said cannula;
    a second hub securely attached to the first end of said cannula;
    whereby said hub and said second hub can be received in respective receiver cavities of an automated biopsy gun, with said interlocking type engagement means in said hub making firm, releasable, interlocking engagement with corresponding interlocking type engagement means associated with the receiver cavity in which said hub is received.

2. Improved core biopsy needle units in accordance with claim 1 wherein said interlocking type engagement means formed in the exposed end of the hub that faces away from the second end of said needle comprises a mortise.

3. Improved core biopsy needle units in accordance with claim 1 wherein said interlocking type engagement means formed in the exposed end of the hub that faces away from the second end of said needle comprises a tenon.

4. Improved core biopsy needle units used with automated biopsy guns, said needle units comprising
    an elongate solid needle having a first and second end;
    a notch formed in the needle nearer said first end of the needle than the second end thereof;
    a hub securely attached to the second end of said needle, said hub having an end facing away from the second end of said needle;
    engagement means comprising a mortise in the end of the hub facing away from the second end of the needle;
    an elongate cannula having a first and second end, with said first end being received over said first end of said needle such that the needle slides longitudinally through said cannula;
    a second hub securely attached to the first end of said cannula;
    an elongated, straight arm whose first end is integrally attached to said hub and whose second end extends away from said hub so that the arm projects from said hub is essentially parallel orientation to the elongate needle extending from said hub;
    means for interlocking the second end of said arm to said second hub to hold said second hub at a fixed distance and at a fixed orientation with respect to said first hub; and
    means associated with said second hub for releasing the interlocking engagement when the second hub is received in a receiver cavity of an automated biopsy gun,
    whereby said hub and said second hub can be received in respective receiver cavities of an automated biopsy gun, with said engagement means in said hub making firm, releasable, interlocking engagement with corresponding engagement means associated with the receiver cavity in which said hub is received.

5. Improved core biopsy needle units in accordance with claim 4 wherein the means for interlocking the second end of said arm to said second hub comprises
    an opening through said second hub through which said arm is received for longitudinal sliding motion through said opening;
    at least one notch on the perimeter of said arm adjacent to the second end of said arm;
    a generally inverted, U-shaped slideway formed in said second hub, said slideway comprising a pair of elongate slots formed in the opposite sides of said second hub and a third slot formed at the top of said second hub interconnecting the pair of slots on the sides of said second hub;

a generally U-shaped slide member that slides in said slideway, said slide member comprising a pair of legs spaced from each other by a base member attached to respective ends of said legs, with the legs of said slide member received in sliding engagement in the pair of elongate slots in said second hub and with the base member of said slide member received in sliding engagement in the third slot formed at the top of said second hub; and an interlock tab on the base member of said U-shaped slide member that engages and interlocks with said notch on the perimeter of said arm when said notch is aligned with said third slot of said slideway and when said U-shaped slide member is slid so that the interlock tab slides into engagement with said notch.

6. Improved core biopsy needle units in accordance with claim 5 wherein the means associated with said second hub for releasing the interlocking engagement of the second end of said arm to said second hub comprises at least one foot member extending downwardly from one of said legs such that when said U-shaped slide member is slid so that the interlock tab slides into engagement with said notch, the foot member extends from a lower side of said second hub, whereby when said second hub is received in a respective receiver cavity of an automated biopsy gun, the foot member extending from the lower side of the second hub is pushed upwardly thereby pushing the U-shaped slide member upwardly so that the interlock tab slides out of engagement with the notch in said arm and the arm can then slide freely in the opening of said second hub.

7. Improved core biopsy needle units used with automated biopsy guns, said needle units comprising an elongate solid needle having a first and second end;

a notch formed in the needle nearer said first end of the needle than the second end thereof;

a hub securely attached to the second end of said needle, said hub having an end facing away from the second end of said needle;

engagement means comprising a tenon in the end of the hub facing away from the second end of said needle;

an elongate cannula having a first and second end, with said first end being received over said first end of said needle such that the needle slides longitudinally through said cannula;

a second hub securely attached to the first end of said cannula;

an elongate, straight arm whose first end is integrally attached to said hub and whose second end extends away from said hub so that the arm projects from said hub in essentially parallel orientation to the elongate needle extending from said hub;

means for interlocking the second end of said arm to said second hub to hold said second hub at a fixed distance and at a fixed orientation with respect to said first hub; and means associated with said second hub for releasing the interlocking engagement when the second hub is received in a receiver cavity of an automated biopsy gun, whereby said hub and said second hub can be received in respective receiver cavities of an automated biopsy gun, with said engagement means in said hub making firm, releasable, interlocking engagement with corresponding engagement means associated with the receiver cavity in which said hub is received.

8. Improved core biopsy needle units in accordance with claim 7 wherein the means for interlocking the second end of said arm to said second hub comprises an opening through said second hub through which said arm is received for longitudinal sliding motion through said opening;

at least one notch on the perimeter of said arm adjacent to the second end of said arm;

a generally inverted, U-shaped slideway formed in said second hub, said slideway comprising a pair of elongate slots formed in the opposite sides of said second hub and a third slot formed at the top of said second hub interconnecting the pair of slots on the sides of said second hub, a generally U-shaped slide member that slides in said slideway, said slide member comprising a pair of legs spaced from each other by a base member attached to respective ends of said legs, with the legs of said slide member received in sliding engagement in the pair of elongate slots in said second hub and with the base member of said slide member received in sliding engagement in the third slot formed at the top of said second hub, and an interlock tab on the base member of said U-shaped slide member that engages and interlocks with said notch on the perimeter of said arm when said notch is aligned with said third slot of said slideway and when said U-shaped slide member is slid so that the interlock tab slides into engagement with said notch.

9. Improved core biopsy needle units in accordance with claim 8 wherein the means associated with said second hub for releasing the interlocking engagement of the second end of said arm to said second hub comprises at least one foot member extending downwardly from one of said legs such that when said U-shaped slide member is slid so that the interlock tab slides into engagement with said notch, the foot member extends from a lower side of said second hub, whereby when said second hub is received in a respective receiver cavity of an automated biopsy gun, the foot extending from the lower side of the second hub is pushed upwardly thereby pushing the U-shaped slide member upwardly so that the interlock tab slides out of engagement with the notch in said arm and the arm can then slide freely in the opening of said second hub.

10. Improved core biopsy needle units used with automated biopsy guns, said needle units comprising an elongate solid needle having a notch formed in the needle nearer said first end of the needle than the second end thereof;

a hub securely attached to the second end of the needle;

an elongate cannula having a first and second end, said first end of said cannula being received over said first end of said needle such that the needle slides longitudinally through said cannula;

a second hub securely attached to the first end of said cannula., an elongate, straight arm whose first end is integrally attached to said hub and whose second end extends away from said hub so that the arm projects from said hub in essentially parallel orientation to the elongate needle extending from said hub;

means for interlocking the second end of said arm to said second hub to hold said second hub at a fixed distance and at a fixed orientation with respect to said first hub, and means associated with said second hub for releasing the interlocking engagement when the second hub is received in a receiver cavity of an automated biopsy gun.

11. Improved core biopsy needle units in accordance with claim 10 wherein the means for interlocking the second end of said arm to said second hub comprises an opening through said second hub through which said arm is received for longitudinal sliding motion through said opening, at least one notch on the perimeter of said arm adjacent to the second end of said arm;

a generally inverted, U-shaped slideway formed in said second hub, said slideway comprising a pair of elongate slots formed in the opposite sides of said second hub and a third slot formed at the top of said second hub interconnecting the pair of slots on the sides of said second hub., a generally U-shaped slide member that slides in said slideway, said slide member comprising a pair Of legs spaced from each other by a base member attached to respective ends of said legs, with the legs of said slide member received in sliding engagement in the pair of elongate slots in said second hub and with the base member of said slide member received in sliding engagement in the third slot formed at the top of said second hub, and an interlock tab on the base member of said U-shaped slide member that engages and interlocks with said notch on the perimeter of said arm when said notch is aligned with said third slot of said slideway and when said U-shaped slide member is slid so that the interlock tab slides into engagement with said notch.

12. Improved core biopsy needle units in accordance with claim 11 wherein the means associated with said second hub for releasing the interlocking engagement of the second end of said arm to said second hub comprises at least one foot member extending downwardly from one of said legs such that when said U-shaped slide member is slid so that the interlock tab slides into engagement with said notch, the foot member extends from a lower side of said second hub, whereby when said second hub is received in a respective receiver cavity of an automated biopsy gun, the foot extending from the lower side of the second hub is pushed upwardly thereby pushing the U-shaped slide member upwardly so that the interlock tab slides out of engagement with the notch in said arm and the arm can then slide freely in the opening of said second hub.

* * * * *